(12) United States Patent
Bell et al.

(10) Patent No.: US 9,676,012 B2
(45) Date of Patent: Jun. 13, 2017

(54) DEVICES FOR TREATING MEDICAL WASTE AND METHODS OF THEIR USE

(71) Applicants: Jeffery Hamilton Bell, Sudbury, MA (US); Andre Philippe Nault, East Longmeadow, MA (US); Robert Todd Winskowicz, North Andover, MA (US); Peter Bates, Framingham, MA (US); Duane Delfosse, Windham, NH (US); Zachary J. Traina, Hingham, MA (US)

(72) Inventors: Jeffery Hamilton Bell, Sudbury, MA (US); Andre Philippe Nault, East Longmeadow, MA (US); Robert Todd Winskowicz, North Andover, MA (US); Peter Bates, Framingham, MA (US); Duane Delfosse, Windham, NH (US); Zachary J. Traina, Hingham, MA (US)

(73) Assignee: SPECTRUM MEDICAL LENDING, LLC, Chicago, IL (US)

( * ) Notice: Subject to any disclaimer, the term of this patent is extended or adjusted under 35 U.S.C. 154(b) by 0 days.

(21) Appl. No.: 14/465,811

(22) Filed: Aug. 21, 2014

(65) Prior Publication Data
US 2016/0051851 A1 Feb. 25, 2016

(51) Int. Cl.
*A61L 2/08* (2006.01)
*A61L 2/00* (2006.01)
*B08B 9/00* (2006.01)
*B09B 3/00* (2006.01)
*A61L 2/07* (2006.01)
*B02C 19/00* (2006.01)

(52) U.S. Cl.
CPC ............. *B09B 3/0075* (2013.01); *A61L 2/07* (2013.01); *B02C 19/0075* (2013.01)

(58) Field of Classification Search
CPC ... A61L 2/00; A61L 11/00; A61L 2/07; B09B 3/0075; B02C 19/0075
USPC ............. 422/1, 26, 295, 306–307; 134/22.15
See application file for complete search history.

(56) References Cited

U.S. PATENT DOCUMENTS 5,427,738 A * 6/1995 Galloway ............... A61L 11/00
241/23

\* cited by examiner

*Primary Examiner* — Monzer R Chorbaji
(74) *Attorney, Agent, or Firm* — James G. Shelnut; JEDA Technologies

(57) ABSTRACT

Disclosed and claimed herein are devices for the treatment of medical waste using high temperature and pressure steam. The devices combine both the sterilization chamber and the steam generating component. The devices may be self-contained and may be movable by one person of average strength and ability. The devices which are self-contained require no special installation, connections, plumbing or permanent or semi-permanent electrical connections. Disclosed and claimed herein are methods using the disclosed and claimed devices.

20 Claims, 3 Drawing Sheets

DEVICES FOR TREATING MEDICAL WASTE AND METHODS OF THEIR USE

FIELD OF THE INVENTION

The present disclosure is in the field of the treatment of medical waste and more particularly in the field of devices and methods for treating medical waste.

BACKGROUND OF THE INVENTION

Current devices and methods for treating medical waste include collecting the waste, storing the waste for a period of time, transporting the waste to a waste treatment center and disposing of the waste by such methods as incineration. Rules relating to the handling of waste differ according to state laws. As a result, medical waste can fester during storage and can be extremely dangerous to handle when collecting, transporting and disposing of such waste. In addition, the movement of medical waste from its point of origin to a storage area exposes handlers, facilities and the environment to potential contamination.

In response to these issues, devices and methods have been described that treat medical waste at the facility in which it is created. The waste is collected and, in some cases stored prior to being placed in the device and essentially sterilized using a number of techniques, either individually or collectively, including chemical treatment, steam autoclaving, microwaving, and ozonation. Disinfecting techniques are also used to treat medical waste. The now treated waste is then collected, packaged, transported and discarded, as the waste is no longer considered, by law, a biological hazard. These devices are generally large, expensive, permanent fixtures which still require collection of the medical waste from the point of origin by personnel which may not be fully trained in the science of infectious waste exposure or emergency procedures needed in the case of a spill or other accident. The operation and maintenance of these devices also require extensive training.

In response to these issues, devices and methods have been described which are smaller and more suitable for being present on hospital floors, in emergency rooms, or in treatment rooms, places where medical waste is generated. Medical waste is collected in red bags, or in sharps containers, until sufficiently full and then transferred to a treatment area and treated to render the waste biologically benign. These devices however generally need special plumbing and/or special electrical power connections. Once installed, these devices are generally intended to remain stationary and are very work intensive to move from one area of need to another area of need. Thus there is an ongoing, unmet need for devices and methods for the treatment of medical waste at the point of origin that is sized to fit readily within a medical environment and can be readily moved by one person of ordinary strength and ability and be self-contained such that no special installation is required for the device to be moved.

Additionally many of the devices and methods that use steam to sterilize medical waste suffer from water build up when the steam is first introduced to the treatment compartment. Attempts to address this issue include providing a steam jacketed treatment compartment for preheating, which adds the complexity and cost of such methods and devices.

SUMMARY OF THE DISCLOSURE

The present disclosure relates to novel self-contained devices for treating medical waste at the point of care which are easily movable, and methods of their use. In a first embodiment, disclosed and claimed herein is a medical waste sterilization and processing device comprising a housing a) at least one ingress in the housing, b) a first sealable compartment comprising a top lid, a central chamber, and a bottom lid, the bottom lid comprising a steam generating component for supplying steam at elevated temperatures and pressures to the compartment and a perforated platform positioned above the steam generating component to support medical waste to be treated, wherein the compartment is capable of maintaining elevated steam temperatures and pressures when sealed, c) a grinder component situated after the first sealable compartment, and d) a second compartment configured to receive treated waste from the first compartment and grinder and capture the waste for removal from at least one egress in the housing.

In a second embodiment disclosed and claimed herein in the device of the above embodiment further comprising a water reclamation component configured to remove excess water and steam from the first sealable compartment and return it to a water reservoir.

In a third embodiment disclosed and claimed herein are the devices of the above embodiments wherein the top lid and bottom lid are removably attached to the central chamber and configured to seal the compartment when attached.

In a fourth embodiment, disclosed and claimed herein are devices of the above embodiment further comprising a component positioned above the first sealable compartment comprising a top segment and a bottom segment, wherein the bottom segment is configured to fit inside the central chamber and move into and out of the central chamber by means of a scissor jack, a piston or an inflation bladder.

In a fifth embodiment, disclosed and claimed herein are devices of the above embodiments wherein the steam generating component in the bottom lid comprises a platform, one or more heating elements, and a water inlet attached to a water reservoir configured to supply water to the heating elements wherein the heating elements are configured to heat the water. In a sixth embodiment, disclosed and claimed herein are devices of the above embodiments, wherein the water reservoir is configured to supply water to the steam generating component, as determined, and receive water from the water reclamation component.

In a seventh embodiment, disclosed and claimed herein are devices of the above embodiments, wherein the water reclamation system comprises a vacuum pump configured to remove at least one of steam or air from the first sealable compartment, a filter to remove at least a portion of particulate matter from the steam, a water reservoir and an optional condenser.

In an eighth embodiment, disclosed and claimed herein are devices of the above embodiments wherein the devices are portable, operate using electrical power as supplied by a wall outlet, are free of fixed attachments requiring installation, further comprise programmable logic systems for user identification and monitoring, measuring, recording and analyzing the time of treatment, the steam temperature and the steam pressure for treatment of the medical waste, the weight of the waste and other user definable data and relaying the data to device controls and log files.

In a ninth embodiment, disclosed and claimed herein are devices of the above embodiments wherein the devices further comprising at least one RFID identification, bar code, or identifying indicia or tracking device provided with the waste output, and/or a quality control system interfaced with the programmable logic system to ensure proper operating parameters.

In a tenth embodiment, disclosed and claimed herein are methods of using the devices of the above embodiments including the steps of a) introducing the medical waste to the first sealable compartment via the inlet, the waste being positioned on the platform, b) sealing the first sealable compartment, c) treating the medical waste by exposing the entire waste load to high temperature steam from about 110° C. to about 150° C. and pressure from about 15 to about 60 psi for at least about 3 minutes, d) moving the treated waste to the grinder for grinding or shredding the treated waste, e) moving the treated waste to a collection area in the second compartment, and f) removing the treated waste from the device.

In an eleventh embodiment, disclosed and claimed herein are methods of using the devices of the above embodiments when appropriately equipped including the steps of a) introducing the medical waste to the first sealable compartment via the inlet, the waste being positioned on the platform, b) sealing the first sealable compartment, c) treating the medical waste by exposing the entire waste load to high temperature steam from about 110° C. to about 150° C. and pressure from about 15 to about 60 psi for at least about 3 minutes, d) moving the treated waste to the grinder for grinding or shredding the treated waste while activating the component positioned above the first sealable compartment wherein the bottom segment, which is configured to fit inside the central chamber, moving down the chamber pushing a substantial portion of the treated waste into the shredder or grinder e) moving the treated waste to a collection area in the second compartment, and f) removing the treated waste from the device.

In a twelfth embodiment, disclosed and claimed herein are methods of the above embodiments wherein the device operates using electrical power as supplied by a wall outlet, the device is free of fixed attachments requiring installation, and/or the device is portable.

DETAILED DESCRIPTION OF THE DISCLOSURE

Figure 1:
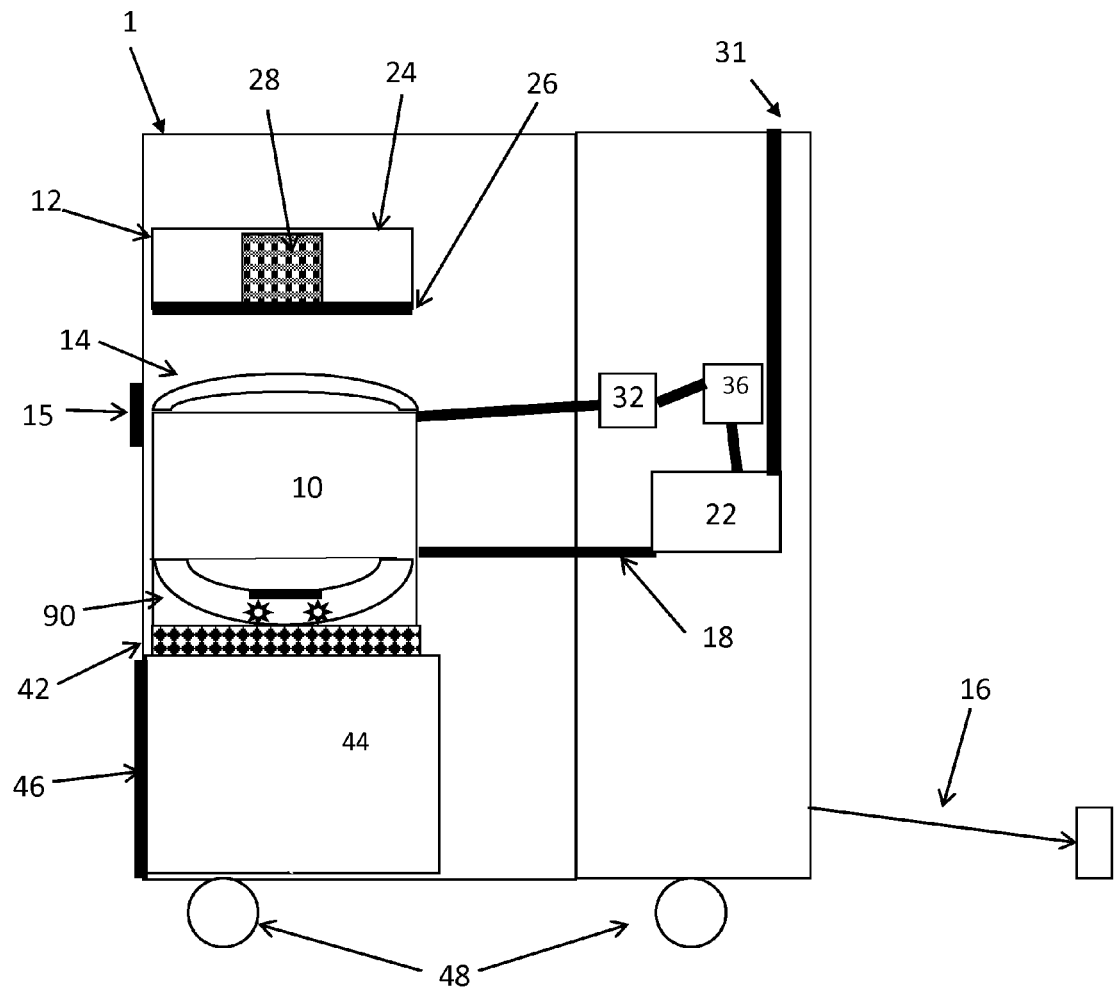
FIG. 1 shows a graphic description of one embodiment device for treatment of medical waste as disclosed and claimed herein.

As used herein, the conjunction "and" is intended to be inclusive and the conjunction "or" is not intended to be exclusive unless otherwise indicated. For example, the phrase "or alternatively" is intended to be exclusive.

As used herein the term sterilization refers to the process of eliminating, or reducing to an acceptable level, infectious materials such as germs, noxious materials, bacteria, viruses and the like, or potentially infectious materials such as blood and other bodily fluids, rendering them harmless.

As used herein the term "installation" refers to permanent or semi-permanent fixtures which require placing devices into position and connecting. The term does not refer to simple plug and unplug of an electrical cord into an electrical outlet.

As used herein the term "medical waste" refers to regulated medical waste, biohazardous waste and potentially infectious waste. It does not relate to pathological waste or chemotherapy, chemical, or hazardous waste.

As used herein the term lid refers to a removable cover, positioned either on the top or on the bottom of a structure.

The current disclosure is intended for all medical waste which requires sterilization to be rendered harmless, including human and animal waste as well as other biological materials found in laboratories or area where work on biologically active materials occurs.

As used herein the terms "grinder", "shredder", "grinding" and "shredding" refer to devices and processes that transform the medical waste into an unrecognizable form through the actions of cutting, slicing, chopping, pulverizing and the like and are used interchangeably.

Disclosed and claimed herein is a medical waste sterilization and processing device having a housing, lids, compartments, grinders, platforms, and other components. They may be made from any structural material known in the art, such as high impact plastic such as, for example, high impact polystyrene, or metals such as, for example, any of a number of types of stainless steel or aluminum. The materials are readily cleanable and do not support the growth or survival of the materials to be sterilized.

The housing is fitted with an ingress allowing materials for treatment to be placed into the device. The ingress may be a sliding door, a lid, or other covered opening and may be provided with a lock, a logging device to measure when materials have been added to the device, or other mechanism to secure the ingress. The ingress may be situated on the top, the side or other area on the device to provide for convenient operation.

The device contains a first sealable compartment to which the ingress is associated, such that waste materials to be treated are placed in the first compartment. The compartment may be constructed of any structural material that can withstand the operational temperatures and pressures of the device. In some embodiments the waste materials reside in a bag specially designed for holding such waste, sometimes called a Red Bag. When the waste bag is input, the bottom is closed to accept the waste, after which the top lid is closed and both lids are secured and the first compartment is sealed. The lids use typical components of gaskets, locks and devices for high pressure sealing well known in the art, so that when high temperature steam is introduced, it is contained within the compartment during the sterilization operation. The compartment is also fitted with sensors to determine time, temperature, and duration of the sterilization processes, which may interface with a programmable logic system.

In some embodiments the top lid slides horizontally to open and close and to allow access to the first compartment.

The bottom lid contains a perforated platform as a top portion of the lid and is positioned above the steam generating component which is situated in the bottom portion of the bottom lid. The perforated platform supports the medical waste to be treated. The perforated platform may be a screen, perforated metal, perforated plastic, or the like containing round holes, squares holes, slots and the like. The platform provides structural integrity to hold the waste, a bag containing waste or a combination, a waste holder, and the like and allow steam to flow through.

Below the perforated platform is the steam generating component containing a heating plate and heating elements which are capable of creating steam when water is introduced to the heating plate of the bottom lid and the heating elements are activated. In some cases the air is significantly evacuated from the first compartment prior to steam generation. When the steam is generated, it flows though the perforations in the perforated platform and permeates the medical waste which is supported thereon. In typical devices, when steam is initially introduced into the first compartment, the compartment is initially cool, so that the introduced steam condenses on the wall of the compartment and collects at the bottom of the compartment, and in and on the medical waste that is to be treated. The steam then must, not only bring the compartment to temperature, but heat the condensed water to become steam in order to properly sterilize the waste. These processes require much more steam than would normally be needed to sterilize a specific amount of waste. Some devices address this issue by requiring the compartment to contain a steam jacket where steam heats the inside walls of the compartment so that the steam introduced into the compartment is less likely to condense. This again requires a large amount of steam to accomplish. Generally a waste treatment device which is permanently installed can be connected to a large, dedicated steam generator connected to the device through a series of high pressure steam pipes. Other devices that have addressed steam condensation require the walls of the first compartment to be heated with electricity. Depending on the size of the device, this is generally a costly solution requiring a complicated compartment configuration as well as causing high energy usage. The current disclosure addresses the condensation by collecting any condensed water onto the heating plate of the bottom lid. When the steam condenses on the walls and collects onto the heated plate, the heated plate reheats the collected water, becoming steam again, which is then recycled into the compartment thus continuing sterilization, allowing for more efficient energy and resource usage. In this manner any steam that enters the compartment will continually be used to sterilize the waste.

Water is initially introduced onto the heating plate from a water reservoir of a water reclamation system.

After the sterilization the first sealable compartment is depressurized and the steam is directed through a filtering system and condensed back into the water reservoir. Water remaining on the heating plate is drained and returned to the reservoir through a filtration system. The reservoir is connected to an inlet which is used to replace water that has been removed with the treated waste when water has reached a low level requiring replenishment. The filter systems used are biofilters, charcoal filter, particle filters and the like, as are well known in the industry for filtering gases and liquids.

After sterilization and removal of residual steam and water the bottom lid can slide laterally while the treated waste, or waste bag, drops into the grinder positioned beneath the first sealable compartment.

The platform may pivotally turn to allow the waste to fall into the grinder or the platform may slide out of the compartment with or without a scraper that scrapes the waste off the platform to fall into grinder. The platform may also be attached to one side of the wall which fall away to allow the waste to proceed to the grinder.

Since the treated waste is typically gravity fed into the grinders, some treated waste may not be heavy enough to fall into the grinder. The devices of the current disclosure may further contain a component which helps the treated waste proceed through to the grinder. The component is positioned above the top lid of the first sealable compartment and comprises a top portion, a bottom portion and a pushing mechanism between the portions. The bottom portion is configured to fit into the central chamber of the first compartment and may be capable of being movably sealed with the chamber. The pushing mechanism may be a scissor jack, an inflatable bladder, a piston, or other device that can push the bottom section through the central chamber and help convey the treated waste to the grinders.

The current disclosure contains grinders and/or shredders which grind the treated waste into small, unrecognizable pieces and is positioned after the first sealable compartment. The grinder may incorporate a planetary gear box which drive a cluster of rotating cutters. The grinding mechanism may be a two stage process wherein the cutting mechanism employs a helical design with helical cutting edges. The grinder may take on any number of configurations including containing a pair of counter-rotating shafts with a plurality of cutter blades or blade knives along the length of the shafts, and a grating plate in which the blade knives rotate, and is not restricted to the kind or type of grinder, or shredder, used. Grinders and shredders suitable for devices of the current disclosure include those well known in the art for grinding medical waste into an unrecognizable form, such as, for example, those disclosed in U.S. Pat. No. 7,195,743 to Butler, incorporated herein by reference, limited to what is disclosed for grinding and shredding of medical waste.

The steam generator component of the currently disclosed device is contained in the bottom lid of the first sealable compartment and is configured to provide steam to the sealable compartment during operation. The steam generating component contains a heating platform and heating elements that are heated by electrical power supplied from a wall outlet and the steam that is generated is conducted through the perforations of the perforated platform to the first sealable compartment. The steam generator component also contains a water reservoir configured to supply water to the steam generator and receive water from the water reclamation system. In some embodiments of the current disclosure there may be water supply pipes connected to the device to supply external water that feeds the steam generating component, such pipes and connections requiring installation and deinstallation when portability is desired. In other embodiments the devices claimed herein may not contain any water supply lines and may be completely self-contained. The removal of the need for installation and deinstallation allows for increased freedom of mobility of the disclosed device not available in other waste treatment devices. The water reservoir may be filled periodically by opening an inlet into the reservoir and filling it to a desired level, determined by the amount of medical waste processed, the efficiency of recycling the excessive water from the treated material and the acceptable amount of water contained in the packaged material.

A water reclamation system may be positioned between the first sealable compartment and the water reservoir. It is configured to substantially remove excess moisture from the first sealable compartment prior to further processing. The first compartment may be heated using electric power to evaporate the excess moisture, the moisture being conducted to a condenser for collection and return to the reservoir. Fans and vacuum may be used to help evacuate moisture from the compartment and/or direct it to water reclamation components such as, for example, condensers cooled by water directed from and returned to the water reservoir. The water reclamation system further may contain purification components such as, for example, HEPA filter, activated carbon filters and the like, situated prior to the water entering the water reservoir. As added precautions, other components may be present to ensure that water returning to the boiler is highly purified, such as, for example, treatment with UVC light radiation and/or ozone.

In this way the steam generating component continually is supplied with water for making steam. The temperature of the steam for sterilization of medical waste is between about 110° C. to about 150° C. and the pressure is between about 15 to about 60 psi. Depending on the amount of waste to be treated and the local regulatory requirements, the time of treatment may run from a minimum of 3 minutes once the waste load has reached 132° C. up to a minimum of 15 minutes at 121° C.

The device may also include a compactor for reducing the volume of the waste situated in the first sealable compartment. The compactor may be driven by a piston, a hinged plate or other compacting device driven by pneumatics, hydraulics or other forms of force.

The device of the current disclosure also contains a second compartment which receives the treated and ground waste from the grinder. The treated waste may be moved to the second compartment by a number of methods including gravity feed or a component designed for helping to convey the treated waste to the grinders, as described supra.

The second compartment may be further configured to package the treated waste. There may be provided a bagging system which accepts the treated waste when moved from the grinder. The bags are designed to withstand the systems heat processes, such as, for example, high density polyethylene, polypropylene or other polyolefin, polystyrene, PET, and the like. When the waste is placed in the bag, the bag may optionally be sealed, heat sealed, or closed in any fashion well known on the art. Substantially all the air may optionally be removed from the bag using a vacuum pump prior to sealing the bag. The bags may contain RFID tags which allow for unique identification of the bag with any number of desired information including, for example the waste producer, the amount of the waste, the levels of treatment, the point of origin, waste types, and the like. The bags may alternatively contain other indicia designed to uniquely identify the bag. The tags may be inherent to the bag or may be added to the bag during processing depending on the desired information needed on the tag. The packaged waste can be removed from an egress positioned in the front, side or back of the device as desired.

The second compartment, as well as the waste bags, may be connected to the water reclamation system so that excessive moisture may be reclaimed at any stage of the process.

In some embodiments of the current disclosure the devices may run on electrical power as obtained from a wall outlet. For example, in North America, northern South America and Japan, electric power is typically supplied at 100-127 V or 220 V, 50-60 Hz to a wall socket. Most of the rest of the world supplies electrical power at 200-240 V, 50-60 Hz to their wall outlets. The current devices may use a typical plug and wire that plugs into the wall and is readily removed. Thus, no special wiring designs or permanent or semi-permanent installation are required. In other embodiments, the device may be hard wired to a power supply.

Some regulations require either longer treatment times or higher temperatures of steam when steam treating the waste, or both. To provide proper treatment the devices of the current disclosure are provided with at least one programmable logic system into which required parameters may be entered, including, for example, steam temperature, steam pressure, time of exposure of the medical waste to the steam, grinding/shredding parameters, unique identifiers of the waste, including the point of origin. The programmable logic system may also record the process information for future reference. Unique identifiers, such as, for example, RFID tags, bar codes, alpha-numeric indicia, or other identifying indicia may be created and attached to the treated waste output.

A radiation detection device may also be included in the device. Waste treatment regulations require that radioactive waste be treated differently from other medical waste, for example, medical waste treated to the level of local requirements may be disposed in a land fill, while waste containing any radioactive waste is barred from such disposal. Thus the device can be used to prevent radioactive waste from being mixed with "regular" medical waste.

In other certain embodiment of the disclosed devices, the device is configured for mobility. As mentioned, the devices may be self-contained and free of external connections. The power supplied to the devices is through a plug into a wall outlet. Wheeling components such as wheels, castors and the like are positioned on the bottom of the device so that the device can be moved from room to room or area to area as desired. The wheeling components may include braking levers which prevent the components from moving until the levers are flipped back freeing the components to allow device movement. The devices in these embodiments are designed so that only one person, of average strength and ability, can move the device. Thus the device is below a weight and dimension that allows the movement of the device by one average person.

The devices of the current disclosure may also include quality control systems which check to calibrate the device and ensure that the various components, compartments and system of the device is in the proper operating condition such that, in operation, the device will provide the required sterilization of the medical waste. The programmable logic device can signal the various components, compartments and systems to provide feedback for operation. The logic device can then signal the operator that the device is working properly or if and where in the device a problem exists.

Methods of treating medical waste using the devices disclosed in any of the above embodiments are disclosed and claimed herein, including the steps of introducing medical waste, which may or may not be contained in a medical waste treatment bag designed for such purposes such as a "Red Bag", into the first sealable compartment of the device via an ingress, supporting the waste onto a perforated platform contained in the bottom lid, treating the medical waste by exposing the waste to high temperature steam and pressure from the steam generating component contained in the bottom lid for a desired length of time with steam at a desired temperature and pressure, the parameters of which may have been preprogrammed into the device using at least one programmable logic system. The first sealable compartment may be evacuated removing a substantial amount of moisture, capturing the moisture by condensing it and routing it back to the steam generating component, optionally compacting the waste. The moisture may proceed through one or more filter components. The bottom lid then retreats so that the waste proceeds to the next step. The top lid may then slide horizontally to allow the component situated above the first sealable compartment to activate, to push the bottom portion of the component through the central chamber and help convey any treated waste to the next step.

The treated medical waste is then conducted through one or more grinder/shredders and into the second compartment. The second compartment is fitted with a bag into which the treated and ground waste is collected. The air may then be optionally substantially removed from the bag, the bag may be sealed, and removed from the device. The bag may be tracked using an RFID tag or other indicia for collection by a solid waste handler, and may be collected as regular solid waste.

The disclosed methods may include programming the required operational parameters into the device using a programmable logic system. These methods may also include a cleansing step after the treatment of medical waste has occurred wherein the first sealable compartment is treated with high temperature steam taken from the steam generating component. The method may also include a quality control step wherein the logic system performs a series of checks to ensure the device is operating properly compared to the programmed parameters.

When the device needs to be moved, the electrical cord is removed from the wall and a person wheels the device to another area and plugs the electrical cord back into an outlet in the other area.

Figure 2:
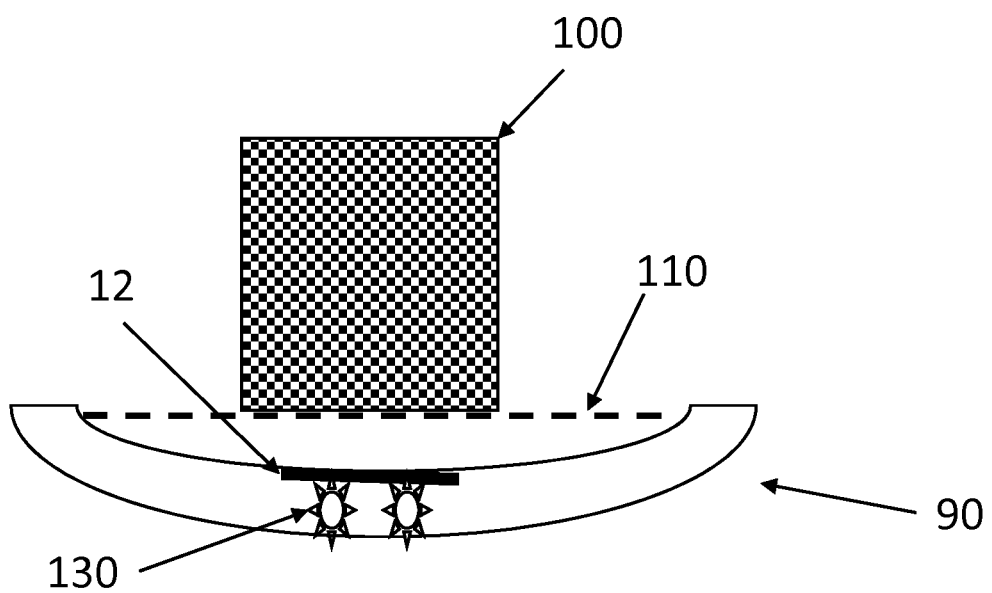
FIG. 2 shows a more detailed graphic description of one component of the device, the bottom lid.

Referring to the figures, FIG. 1 depicts a graphic representation of one embodiment of the disclosure. The device contains a housing 1, a first sealable compartment 10, a conveying component 12, a top lid 14, and a bottom lid 90, a more detailed cut-away depiction of the bottom cover is shown in FIG. 2. An inlet 15 allows medical waste to be introduced into the compartment 10. The depicted device runs on electricity obtained from an electrical wall socket using an electrical cord 16. A water reservoir 22, having a water outlet 18 supplies water to the steam generating component in the bottom lid 90. An evacuation pump 36 is connected to the first sealable chamber 10 for drawing air and/or excess moisture out of the chamber, through a filter mechanism 32 and back into the water reservoir 22. A water replenishment inlet 31 is connected to the reservoir to externally supply water as needed. One or more grinding/shredding devices 42 are provided between the first compartment 10 and the second compartment 44. After waste is collected in a bag, the bag is removed through egress 46. The device may be portable and movable in which case medical grade castors are used 48. The conveying component 12 is shown with a top portion 24, a bottom portion 26, and a means 28 for moving the bottom portion in and out of the chamber. FIG. 2 shows a graphic depiction of the bottom lid in a cut-away view 90. A bag containing the medical waste to be treated 100 is positioned on the perforated platform 110. Water (not shown) sits on the heating plate 120 which is situated above the heating elements 130. Water collects, or is input, onto the heating plate and turned into steam by the heating elements. The steam flows through the perforations in the perforated platform to sterilize the medical waste contained in the bag.

Figure 3:
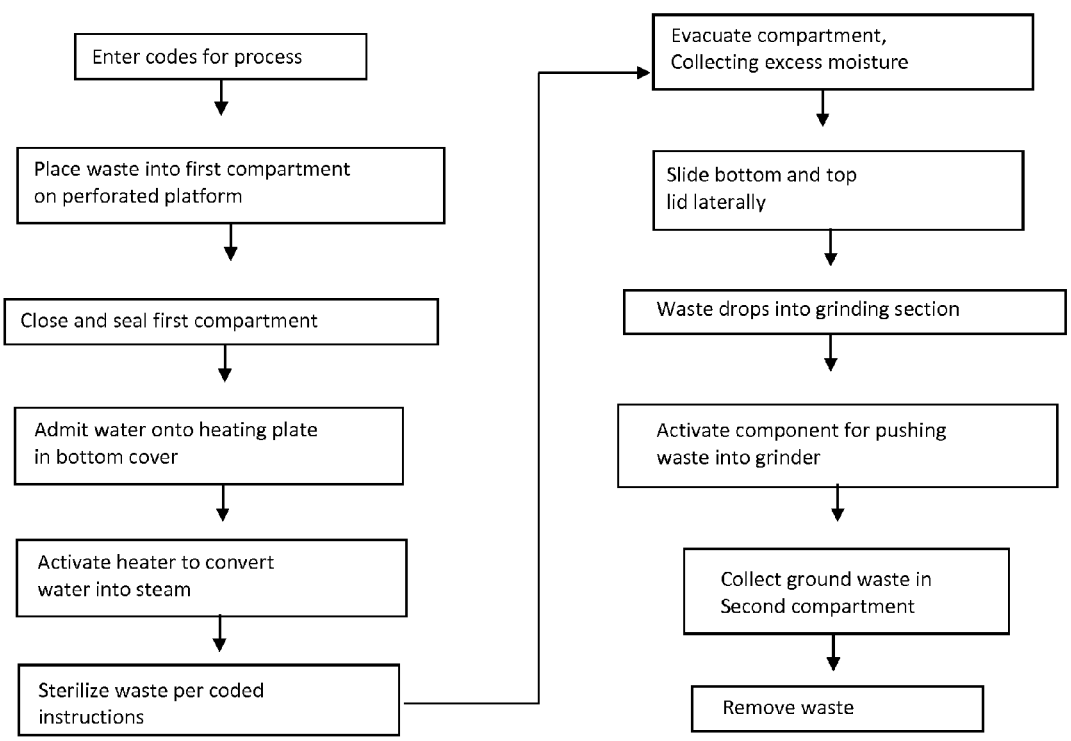
FIG. 3 shows a flow chart of one embodiment method disclosed and claimed herein.

FIG. 3 depicts one embodiment of the process flow claimed and described herein.

We claim:

1. A medical waste sterilization and processing device comprising a housing comprising:
   a. at least one ingress in the housing,
   b. a first sealable compartment comprising:
      i. a top lid,
      ii. a central chamber, and
      iii. a bottom lid comprising a steam generating component for supplying steam at elevated temperatures and pressures to the compartment, and a perforated platform positioned above the steam generating component to support medical waste to be treated, wherein the compartment is capable of maintaining elevated steam temperatures and pressures when sealed,
   c. a grinder component situated after the first sealable compartment, and
   d. a second compartment configured to receive the treated waste from the first compartment and grinder and capture the waste for removal from at least one egress in the housing.

2. The device of claim 1, wherein the top lid and bottom lid are removably attached to the central chamber and configured to seal the compartment when attached.

3. The device of claim 1, further comprising a water reclamation component configured to remove excess water and steam from the first sealable compartment and return it to a water reservoir.

4. The device of claim 3, wherein the water reservoir is configured to supply water to the steam generating component as determined and receive water from the water reclamation component.

5. The device of claim 3, wherein the water reclamation system comprises a vacuum pump configured to remove at least one of air or steam from the first sealable compartment, a filter to remove at least a portion of particulate matter from the steam, a water reservoir and optionally a condenser.

6. The device of claim 1, further comprising a conveying component positioned above the first sealable compartment comprising a top segment and a bottom segment, wherein the bottom segment is configured to fit inside the central chamber and move into and out of the central chamber by means of a scissor jack, a piston or an inflation bladder.

7. The device of claim 1, wherein the steam generating component in the bottom lid comprises a platform, one or more heating elements, and a water inlet attached to a water reservoir configured to supply water to the heating elements wherein the heating elements are configured to heat the water.

8. The device of claim 1, wherein the device operates using electrical power as supplied by a wall outlet.

9. The device of claim 1, wherein the device is free of fixed attachments requiring installation.

10. The device of claim 1, wherein the device is portable.

11. The device of claim 1, further comprising a programmable logic system for user identification and monitoring, measuring, recording and analyzing the time of treatment, the steam temperature and the steam pressure for treatment of the medical waste, the weight of the waste and other user definable data and relaying the data to device controls and log files.

12. The device of claim 1, further comprising at least one RFID identification, bar code, or identifying indicia or tracking device provided with the waste output.

13. The device of claim 1, further comprising a quality control system interfaced with the programmable logic system to ensure proper operating parameters.

14. The device of claim 1 wherein the waste output is vacuum heat sealed prior to removal.

15. A method of treating medical waste comprising the steps of:
   a. obtaining the device of claim 1,
   b. introducing the medical waste to the first sealable compartment via the inlet, the waste being positioned on the platform,
   c. sealing the first sealable compartment,
   d. treating the medical waste by exposing the entire waste load to high temperature steam from about 110° C. to about 150° C. and pressure from about 15 to about 60 psi for at least about 3 minutes,
   e. grinding or shredding the treated waste, f. moving the treated waste to a collection area in the second compartment, and g. removing the treated waste from the device.

16. The method of claim 15, wherein the device operates using electrical power as supplied by a wall outlet.

17. The method of claim 15, wherein the device is free of fixed attachments requiring installation.

18. A method of treating medical waste comprising the steps of:

a. obtaining the device of claim 6, b. introducing the medical waste to the first sealable compartment via the inlet, the waste being positioned on the platform, c. sealing the first sealable compartment, d. treating the medical waste by exposing the entire waste load to high temperature steam from about 110° C. to about 150° C. and pressure from about 15 to about 60 psi for at least about 3 minutes, e. moving the treated waste to the grinder for grinding or shredding the treated waste, while activating the conveying component positioned above the first sealable compartment wherein the bottom segment, which is configured to fit inside the central chamber, moves down the chamber pushing a substantial portion of the treated waste into the grinder, f. moving the treated waste to a collection area in the second compartment, and g. removing the treated waste from the device.

19. The method of claim 18, wherein the device operates using electrical power as supplied by a wall outlet.

20. The method of claim 18, wherein the device is free of attachments requiring installation.

* * * * *